(12) United States Patent
Li et al.

(10) Patent No.: US 9,399,024 B2
(45) Date of Patent: Jul. 26, 2016

(54) KONJAC FORMULATION AND METHOD FOR PREPARING THE SAME

(71) Applicant: WEIFANG HUIRUN FOOD CO., LTD., Weifang (CN)

(72) Inventors: Quanjin Li, Weifang (CN); Huchang Chen, Weifang (CN)

(73) Assignee: SHANDONG HEARUN DIETARY HALL CO., LTD., Weifang (CN)

(*) Notice: Subject to any disclaimer, the term of this patent is extended or adjusted under 35 U.S.C. 154(b) by 73 days.

(21) Appl. No.: 14/536,706

(22) Filed: Nov. 10, 2014

(65) Prior Publication Data

US 2015/0064244 A1 Mar. 5, 2015

Related U.S. Application Data

(63) Continuation-in-part of application No. PCT/CN2013/000537, filed on May 7, 2013.

(30) Foreign Application Priority Data

May 8, 2012 (CN) .......................... 2012 1 0139116

(51) Int. Cl.

| | |
|---|---|
| *A61K 36/888* | (2006.01) |
| *A61K 36/899* | (2006.01) |
| *A61K 33/26* | (2006.01) |
| *A61K 31/4415* | (2006.01) |
| *A61K 31/51* | (2006.01) |
| *A61K 31/525* | (2006.01) |
| *A61K 31/714* | (2006.01) |
| *A61K 31/375* | (2006.01) |
| *A61K 9/48* | (2006.01) |
| *A23L 1/302* | (2006.01) |
| *A23L 1/304* | (2006.01) |
| *A23L 1/30* | (2006.01) |
| *A23L 1/308* | (2006.01) |
| *A23L 1/0522* | (2006.01) |
| *A61K 36/88* | (2006.01) |
| *A61K 45/06* | (2006.01) |

(52) U.S. Cl.
CPC .............. *A61K 9/4875* (2013.01); *A23L 1/0522* (2013.01); *A23L 1/3002* (2013.01); *A23L 1/302* (2013.01); *A23L 1/304* (2013.01); *A23L 1/308* (2013.01); *A61K 9/48* (2013.01); *A61K 9/4833* (2013.01); *A61K 9/4866* (2013.01); *A61K 31/375* (2013.01); *A61K 31/4415* (2013.01); *A61K 31/51* (2013.01); *A61K 31/525* (2013.01); *A61K 31/714* (2013.01); *A61K 33/26* (2013.01); *A61K 36/88* (2013.01); *A61K 36/888* (2013.01); *A61K 36/899* (2013.01); *A61K 45/06* (2013.01)

(58) Field of Classification Search
CPC ... A61K 36/888; A61K 36/899; A61K 33/26; A61K 31/4415; A61K 31/51; A61K 31/525; A61K 31/714; A61K 31/375; A61K 9/48
See application file for complete search history.

(56) References Cited

FOREIGN PATENT DOCUMENTS

CN        1943685 A    * 4/2007

OTHER PUBLICATIONS

PTO translation of foreign priority document CN 201210139116.4.*

* cited by examiner

*Primary Examiner* — John Pak
*Assistant Examiner* — Nathan W Schlientz
(74) *Attorney, Agent, or Firm* — Matthias Scholl, PC; Matthias Scholl

(57) ABSTRACT

A konjac formulation in the form of a capsule, including between 85 and 95 parts by weight of konjac gum, between 5 and 10 parts by weight of black rice, between 0.5 and 2 parts by weight of biological Fe, and between 0.5 and 2 parts by weight of vitamin.

3 Claims, No Drawings

KONJAC FORMULATION AND METHOD FOR PREPARING THE SAME

CROSS-REFERENCE TO RELATED APPLICATIONS

This application is a continuation-in-part of International Patent Application No. PCT/CN2013/000537 with an international filing date of May 7, 2013, designating the United States, now pending, and further claims priority benefits to Chinese Patent Application No. 201210139116.4 filed May 8, 2012. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

1. Field of the Invention

The invention relates to a konjac formulation in the form of a capsule and a method for preparing the same.

2. Description of the Related Art

*Amorophophallus Konjac* is a perennial herb of Araceae, and exhibits a certain therapeutic effect to hypertension, obesity, diabetes, constipation. Conventional drugs for treating diabetes, including Chinese medicine products and chemical synthesis products, both contain no soluble cellulose (hydrophilic), thereby resulting in unsatisfactory therapeutic effect. In addition, the complication is prone to occur when patients are administered with the drugs over a long period of time.

SUMMARY OF THE INVENTION

In view of the above-described problems, it is one objective of the invention to provide a konjac formulation in the form of a capsule and a preparation method thereof. The major component of the konjac formulation is konjac gum which has a viscosity reaching 35 thousand centipoises thereby being difficult for encapsulation. The addition of black rice makes the encapsulation practicable, and the resulting capsule is convenient for use and has good health effect.

To achieve the above objective, in accordance with one embodiment of the invention, there is provided a konjac formulation in the form of a capsule, comprising between 85 and 95 parts by weight of konjac gum, between 5 and 10 parts by weight of black rice, between 0.5 and 2 parts by weight of biological Fe, and between 0.5 and 2 parts by weight of vitamin.

In a class of this embodiment, the konjac formulation comprises 90 parts by weight of konjac gum, 8 parts by weight of black rice, one part by weight of biological Fe, and one part by weight of vitamin.

The konjac gum is made of a hydrogel-like compound polysaccharide extracted from tuber of konjac, which is actually a high molecular weight nonionic konjac glucomannan (KGM) having low-calorie, low-protein, high dietary fibers. The granules of the konjac gum swell in water, and break to release KGM polymers.

In certain embodiments of the invention, the konjac gum operates to supply nutrients for the pancreatic beta cells, improve the sensitivity of the pancreatic beta cells, and reduce the metabolic burden on the pancreatic islet, so as to gradually recover the function of the pancreatic islet, prompt the normal secretion of insulin and C-peptide, and ultimately achieve a stable equilibrium state.

The black rice is a kind of glutinous rice that has medicinal and edible values, which is a special variety of paddy. In this invention, the black rice is fried in a pan at 400° C. for between 20 and 25 min, and then ground to a fineness of 100 meshes. The black rice functions as a stabilizing agent and an additive for supplementing the molecules of iron so that the konjac gum can swell by 100 folds rapidly. In the prior art, the konjac gum absorbs water quickly at 40-50° C. and then solidifies to form an expansion layer, which impedes the expansion of the konjac gum.

In a class of this embodiment, the biological Fe is an iron element extracted from animal blood, which functions as a nutritious supplement.

In a class of this embodiment, the vitamin is a mixture of vitamin B and vitamin C with a mass ratio thereof of 1:1, which functions to resist the inflammation.

In another aspect, the invention provides a method for preparing a konjac formulation in the form of a capsule, the method comprising:

1) weighing the konjac gum, the black rice, the biological Fe, and the vitamin according to corresponding parts by weight, frying the black rice in a pan at 400° C. for between 20 and 25 min, grinding the black rice to a fineness of 100 meshes, the vitamin being a mixture of vitamin B and vitamin C with a mass ratio thereof of 1:1;
2) uniformly mixing the above-mentioned materials; and
3) encapsulating uniformly mixed materials in step 2) using a capsule filling equipment to yield a capsule product.

Different from conventional health products, the konjac formulation in the form of a capsule can supply nutrients for the pancreatic beta cells, so that the pancreatic islet can gradually recover to normal state, produce sufficient insulin and C-peptide to meet the metabolic demands, and ultimately achieve a stable equilibrium state. The capsule contains soluble dietary fibers, which are one of the key nutrients for the pancreatic beta cells.

Based on the nutriology theory, the konjac formulation in the form of a capsule is rich in complex polysaccharides, amino acids, vitamins and trace minerals, and can regulate immune function, enhance non-specific immunity, cellular immunity, humoral immunity, or all of them. The dietary fibers of the konjac gum have the largest viscosity, are not digested and absorbed, contain no calories, but can provide a sense of satiety, and can reduce and delay the absorption of glucose. The dietary fibers are fermented in the colon propionate to produce absorbable propionates, stimulate the liver cells to accelerate glycolysis, reduce free fatty acid in the blood circulation, increase the sensitivity of the pancreatic beta cells, induce impaired glucose tolerance, thereby ultimately achieving the objectives of health care and therapy for patients with diabetes.

Table 1 shows the test result of blood lipid of a patient before and after being administered with the konjac formulation in the form of a capsule.

TABLE 1

| Biochemical indicator | Before testing | | After testing | |
|---|---|---|---|---|
| | n | m ± SD | n | m ± SD |
| FBG (mg/%) | 72 | 159.53 ± 36.12 | 61 | 139.52 ± 35.82 |
| PBG (mg/%) | 72 | 275.72 ± 80.32 | 61 | 227.67 ± 59.10 |

TABLE 1-continued

|  | Before testing | | After testing | |
|---|---|---|---|---|
| Biochemical indicator | n | m ± SD | n | m ± SD |
| GBb (nmol fructose 10 mgHb) | 71 | 91.68 ± 21.76 | 27 | 77.93 ± 17.83 |
| TC (mg/%) | 69 | 206.94 ± 42.14 | 61 | 195.38 ± 32.88 |
| TG (mg/%) | 69 | 166.13 ± 98.25 | 61 | 139.59 ± 72.31 |
| HDL-C (mg/%) | 69 | 58.23 ± 11.92 | 61 | 59.18 ± 11.79 |
| LDL-C (mg/%) | 69 | 115.49 ± 35.11 | 61 | 108.30 ± 28.16 |

According to the test results, the konjac formulation can significantly reduce the blood glucose of a diabetes patient.

Advantages according to embodiments of the invention are summarized as follows: the konjac formulation is made of natural materials without any addition of hormones, so it is medicinal and edible, and causes no side effect. The capsule can effectively prevent and treat diabetes, and produce no complication. The method for preparing the capsule is simple, the production cost is low, and the resulting capsule is easy to carry and convenient for administration.

DETAILED DESCRIPTION OF THE EMBODIMENTS

For further illustrating the invention, experiments detailing a konjac formulation in the form of a capsule and a method for preparing the same are described below. It should be noted that the following examples are intended to describe and not to limit the invention.

Example 1

A konjac formulation in the form of a capsule comprises 85 g of konjac gum, 5 g of black rice, 0.5 g of biological Fe, and 0.5 g of vitamin.

The konjac gum is purchased from Chengdu Sheng Te Meng Konjac Powder Co., Ltd.

The black rice has a fineness of 100 meshes.

The biological Fe is Fe-rich capsules manufactured by Tianjin Strong's Health Products Co., Ltd., with a grain size of 1000-2000 meshes.

The vitamin is a mixture of vitamin B and vitamin C with a mass ratio thereof of 1:1.

Example 2

A konjac formulation in the form of a capsule comprises 95 g of konjac gum, 10 g of black rice, 2 g of biological Fe, and 2 g of vitamin.

The konjac gum is purchased from Chengdu Sheng Te Meng Konjac Powder Co., Ltd.

The black rice has a fineness of 100 meshes.

The biological Fe is Fe-rich capsules manufactured by Tianjin Strong's Health Products Co., Ltd., with a grain size of 1000-2000 meshes.

The vitamin is a mixture of vitamin B and vitamin C with a mass ratio thereof of 1:1.

Example 3

A konjac formulation in the form of a capsule comprises 90 g of konjac gum, 8 g of black rice, 1 g of biological Fe, and 1 g of vitamin.

The konjac gum is purchased from Chengdu Sheng Te Meng Konjac Powder Co., Ltd.

The black rice has a fineness of 100 meshes.

The biological Fe is Fe-rich capsules manufactured by Tianjin Strong's Health Products Co., Ltd., with a grain size of 1000-2000 meshes.

The vitamin is a mixture of vitamin B and vitamin C with a mass ratio thereof of 1:1.

Example 4

A method for preparing a konjac formulation in the form of a capsule of Examples 1-3, comprises:

1) weighing the konjac gum, the black rice, the biological Fe, and the vitamin according to corresponding parts by weight, frying the black rice in a pan at 400° C. for between 20 and 25 min, grinding the black rice to a fineness of 100 meshes, the vitamin being a mixture of vitamin B and vitamin C with a mass ratio thereof of 1:1;

2) uniformly mixing the above-mentioned materials; and 3) encapsulating uniformly mixed materials in step 2) using a capsule filling equipment to yield a capsule product.

Example 5

Table 2 shows the improvement of diabetes patient after being administered with the konjac formulation in the form of a capsule in Example 1 for 65 consecutive days.

TABLE 2

| Symptom | Number of case | Consumption (g/day) | Improved number of case | Improvement rate |
|---|---|---|---|---|
| Bulimia | 35 | 4 | 31 | 88.6 |
| Nocturia | 53 | 4 | 48 | 90.6 |
| Polydipsia | 28 | 4 | 23 | 82.1 |
| Constipation | 35 | 4 | 34 | 97.1 |
| Watery stool | 9 | 4 | 8 | 88.9 |

Example 6

Table 3 shows the improvement of diabetes patient after being administered with the konjac formulation in the form of a capsule in Example 2 for 65 consecutive days.

TABLE 3

| Symptom | Number of case | Consumption (g/day) | Improved number of case | Improvement rate |
|---|---|---|---|---|
| Bulimia | 40 | 4 | 36 | 90.0 |
| Nocturia | 50 | 4 | 47 | 94.0 |
| Polydipsia | 35 | 4 | 31 | 88.6 |
| Constipation | 45 | 4 | 44 | 97.8 |
| Watery stool | 11 | 4 | 10 | 90.9 |

Example 7

Table 4 shows the improvement of diabetes patient after being administered with the konjac formulation in the form of a capsule in Example 3 for 65 consecutive days.

TABLE 4

| Symptom | Number of case | Consumption (g/day) | Improved number of case | Improvement rate |
|---|---|---|---|---|
| Bulimia | 70 | 4 | 60 | 85.7 |
| Nocturia | 51 | 4 | 45 | 88.2 |
| Polydipsia | 35 | 4 | 29 | 82.9 |

TABLE 4-continued

| Symptom | Number of case | Consumption (g/day) | Improved number of case | Improvement rate |
|---|---|---|---|---|
| Constipation | 30 | 4 | 28 | 93.3 |
| Watery stool | 15 | 4 | 13 | 86.7 |

Unless otherwise indicated, the percentages involved in this invention are all weight percentages.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A pharmaceutical composition comprising 85-95% by weight of konjac gum, 5-10% by weight of black rice, 0.5-2% by weight of biological iron extracted from animal blood, and 0.5-2% by weight of a mixture of vitamin B and vitamin C, wherein the mass ratio of vitamin B to vitamin C is 1:1, and the composition is in the form of a capsule.

2. The composition of claim 1 comprising 90% by weight of konjac gum, 8% by weight of black rice, 1% by weight of biological iron, and 1% by weight of a mixture of vitamin B and vitamin C.

3. A method for preparing the pharmaceutical composition of claim 1, the method comprising:
   1) weighing konjac gum, black rice, biological iron, vitamin B and vitamin C; wherein the biological iron has been extracted from animal blood;
   2) uniformly mixing the materials from step 1) wherein the mixture comprises 85-95% by weight of konjac gum, 5-10% by weight of black rice, 0.5-2% by weight of biological iron, and 0.5-2% by weight of a mixture of vitamin B and vitamin C in a mass ratio of 1:1; and
   3) encapsulating the uniformly mixed materials from step 2) within a capsule.

* * * * *